US 6,576,781 B2

(12) United States Patent
Corey

(10) Patent No.: US 6,576,781 B2
(45) Date of Patent: *Jun. 10, 2003

(54) SYNTHESIS OF PSEUDOPTEROSIN COMPOUNDS

(75) Inventor: Elias J. Corey, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/893,333

(22) Filed: Jun. 27, 2001

(65) Prior Publication Data

US 2002/0058698 A1 May 16, 2002

Related U.S. Application Data

(63) Continuation-in-part of application No. 09/712,884, filed on Nov. 15, 2000, now Pat. No. 6,423,877.

(51) Int. Cl.$^7$ .......................... C07F 7/06; C07C 309/00

(52) U.S. Cl. .......................... 556/486; 558/57

(58) Field of Search ............... 556/486; 558/57

(56) References Cited

PUBLICATIONS

Fenical, "Marine Soft Corals of the Genus Pseudopterogorgia: A Resource for Novel Anti–Inflammatory Diterpenoids", *Journal of Natural Products*, vol. 50, No. 6, pp. 1001–1008, Nov.–Dec. 1987.

Look et. al., "The Seco–Pseudopterosins, New Anti–Inflammatory Diterpene–Glycosides From a Caribbean Gorgonian Octocoral of the Genus *Pseudopterogorgia*", *Tetrahedron*, vol. 43, No. 15, pp. 3363 to 3370, 1987.

McCombie et. al., "Controlling Benzylic and Anomeric Functionality and Stereochemistry: Methodology and Syntheses Utilising Intramolecular Ionic Hydrogenation", Schering–Plough Research Institute *Synlett*, 8–93, pp. 541–547.

Look et. al., "The Pseudopterosins: A New Class of Anti-inflammatory and Analgesic Diterpene Pentosides from the Marine Sea Whip *Pseudopterogorgia elisabethae* (Octocorallia)", *J. Org. Chem. 1986*, 51, 5140–5145.

(List continued on next page.)

*Primary Examiner*—Samuel Barts
*Assistant Examiner*—Paul A. Zucker
(74) *Attorney, Agent, or Firm*—Ernest V. Linek; Banner & Witcoff, Ltd.

(57) ABSTRACT

The present invention is directed to the synthetic processes outlined in Schemes 1, 2 and 3, to the novel intermediates recited therein, and to the uses of these compounds as synthetic precursors to the pseudopterosins. Other embodiments and aspects of the present invention include the novel synthetic procedures described herein. Scheme I is shown below:

6 Claims, 2 Drawing Sheets

OTHER PUBLICATIONS

Ranu et. al., "Surface–mediated Solid Phase Reaction. Part 6. [1] Mukaiyama–Michael Addition of Silyl Enol Ethers to Alkyl Vinyl Ketones on the Surface of Alumina: a Simple and Convenient Method for the Synthesis of 1,5–Diketones", *J. Chem. Soc. Perkin Trans.* 1 1994.

Brown et. al., "Thexylborane as a Convenient Reagent for the Cyclic Hydroboration of Dienes. Stereospecific Syntheses via Hydroboration", *J. Am. Chem. Soc. 89*:21 Oct. 11, 1967.

Heathcock et. al., "Stereoselection in the Michael Addition Reaction. 1. The Mukaiyama–Michael Reaction[1]", *J. Am. Chem. Soc. 1985*, 107, 2797–2799.

Look et. al., "The pseudopterosins: Anti–inflammatory and analgesic natural products from the sea whip *Pseudopterogorgia elisabethae*" *Proc. Natl. Acad. Sci. USA* vol. 83, pp. 6238–6240, Sep. 1986 Chemistry.

Corey et. al., "Optical Rotation and Helical Polypeptide Chain Configuration in $_a$–Proteins", *J. Am. Chem. Soc.* vol. 79 pp. 248 1957.

Gill et. al., "A synthetic approach to the pseudopterosins", *Chem. Commun.*, 1996.

LeBrazidec et. al., "Synthetic approaches to pseudopterosin G aglycone dimethyl ether", *J. Chem. Soc., Perkin Trans. 1*, 1998.

Narasaka et. al., "The Michael Reaction of Silyl Enol Ethers with a, β–Unsaturated Ketones and Acetals in the Presence of Titanium Tetraalkoxide and Titanium Tetrachloride", *Bulletin of the Chem. Soc. of Japan*, vol. 49(3), 779–783 (1976).

Corey et. al., "The Application of a Mechanistic Model Leads to the Extension of the Sharpless Asymmetric Dihydroxylation to Allylic 4–Methoxybenzoates and Conformationally Related Amine and Homoallylic Alcohol Derivatives", *J. Am. Chem. Soc.* 1975, 117, 10805–10816.

Deslongchamps et. al., "The total synthesis of (+)–ryanodol. Part II. Model studies for rings B and C of (+)–anhydroryanodol. Preparation of a key pentacyclic intermediate", *Can. J. Chem.* vol. 68, 1990.

Sodeoka et. al., "Highly Efficient Synthesis of Carbacyclin Analogue, Stereospecific Synthesis of Aryl–Substituted Exocyclic Olefin", *J. Am. Chem. Soc.* 1988, 110, 4823–4824.

Corey et. al., "Enantiospecific Total Synthesis of Pseudopterosins A and E", *J. Am. Chem. Soc.* 1989, 111, 5472–5474.

Vedeja et. al., "An E–Selective 1,3–Diene Synthesis from Moderated Ylides and Aldehydes", *J. Org. Chem.* 1984, 49, 210–212.

Broka et. al., "Total Synthesis of (−)–Pseudopterosin A" *J. Org. Chem.* 1988, 53, 1584–1586.

Anelli et. al., "Oxidation of Diols with Alkali Hypochlorites Catalyzed by Oxammonium Salts under Two–Phase Conditions" *J. Org. Chem.* 1989, 54, 2970–2972.

Brown et. al., "Boraheterocycles Via Cyclic Hydroboration", *Tetrahedron* vol. 33, pp. 2331–2357.

Corey et. al., "A New Enantiospecific Route to The Pseudopterosins", *Tetrahedron Letters*, vol. 31, No. 27, pp. 3857–3858, 1990.

Stevens et. al., "Further Studies on the Utility of Sodium Hypochlorite in Organic Synthesis. Selective Oxidation of Diols and Direct Conversion of Aldehydes to Esters", *Tetrahedron Letters*, vol. 23, No. 45, pp. 4647–4650, 1982.

McCombie et. al., "Controlling Benzylic Functionality and Stereochemistry: 1. Synthesis of the Secopseudopterosin Aglycone", *Tetrahedron Letters*, vol. 32, No. 19, pp. 2083–2086. 1991.

Majdalani et. al., "Chiral $\eta^6$–Arene–Cr(CO)$_3$ Complexes in Organic Synthesis: A Short and Highly Selective Synthesis of the 18–nor–seco–Pseudopterosin Aglycone", *Tetrahedron Letters* vol. 38, No. 26, pp. 4545–4548, 1997.

Majdalani et. al., "Enantioselective Synthesis of the Aglycones of Pseudopterosin and seco–Pseudopterosin via a Common Synthetic Intermediate", *Synlett.* 1997 pp. 1303–1305.

Terao et. al., "A Facile Synthesis of Allylic Alcohols", *Synthesis* 1979 pp. 467–468.

Cristau et. al., "Synthesis of Diphenyldialkylphosphonium Salts", *Synthesis* 1988 pp. 911–912.

Buszek et. al., "Total Synthesis of Pseudopterosin A and E Aglycon", *Tetrahedron Letters* vol. 36, No. 50, pp. pp. 9129–9132, 1995.

Buszek, "First Intramolecular Benzyne Diels–Alder Reaction with an Acyclic Diene. Unusual Effect of Diene Geometry on the Course of the Reaction", *Tetrahedron Letters*, vol. 36, No. 50, pp. 9125–9128, 1995.

Rouhi, "Supply Issues Complicate Trek of Chemicals From Sea to Market", *Chem. Eng. News*, Nov. 20, pp. 42–44.

Mashraqui et. al., "Active MnO$_2$. Oxidative Dehydrogenations", *Synth. Commun.* 1982, vol. 12, pp. 637–645.

Corey et al., "A Direct and Efficient Steriocontrolled Synthetic Route to the Pseudopterosins, Potent Marine Antiinflammatory Agents", *J. Am. Chem. Soc*, 1998, vol. 120, pp. 12777–12782.

Danishefsky et al., "The Reaction of Enamines with Activated Butadienes. A One–Step Synthesis of Benzenes", *J. Org. Chem.* vol. 30, 1965, pp. 3676–3679.

Leffingwell et al., "A New Synthetic Method for the Preparation of Aromatic Aldehydes, Ketones, and Schiff Bases", *J. Chem. Soc. Chem. Comm.*, 1969, pp. 1151–1152.

Milos Hudlicky, "Oxidations in Organic Chemistry", *Am. Chem. Soc.*, 1990, pp. 32–33.

SYNTHESIS OF PSEUDOPTEROSIN COMPOUNDS

CROSS-REFERENCE TO RELATED APPLICATION

This application is a continuation-in-part of copending application Ser. No. 09/712,884, filed Nov. 15, 2000, now U.S. Pat. No. 6,423,877, the disclosure of which is hereby incorporated herein by reference.

STATEMENT OF GOVERNMENT SUPPORT

This invention was supported in part by funding received from the National Science Foundation, Grant No. CHE9300276 and from the National Institutes of Health, Grant No. GM34167. Thus, the Government of the United States has certain rights in this invention.

BACKGROUND OF THE INVENTION

The pseudopterosins are compounds produced by the Caribbean sea whip *Pseudopteragoria elisabethae*. These compounds are exemplified by the compounds pseudopterosin A and E which are remarkably active anti-inflammatory agents that were discovered by W. Fenical and collaborators.

In copending application Ser. No. 09/712,884 there is reported an especially simple and direct route for the synthesis of anti-inflammatory pseudopterosins such as pseudopterosin A (1) and pseudopterosin E (2) from inexpensive (S)-(−)-limonene.[1]

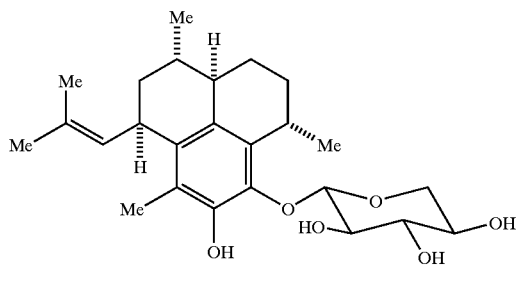

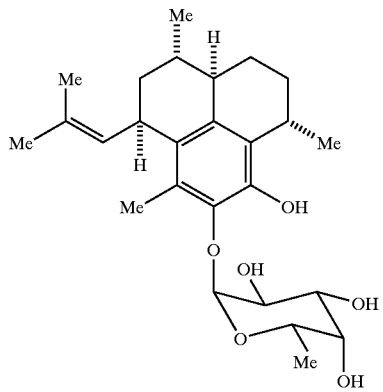

The synthetic strategy used involved an aromatic annulation process to form the benzenoid ring and a cationic cyclization to generate the third ring of the aglycone intermediate 3.[2]

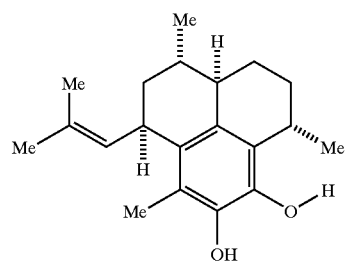

An interesting discovery made in connection with the initial work was the finding that either the pseudopterosin A-F system or the C (1)-diastereomeric analogs could be accessed depending on the intermediate used for the cationic closure of the third ring. The present invention is directed to that discovery.

SUMMARY OF THE INVENTION

As shown in Scheme 1, ring closure of the mesylate 4 produced the pseudopterosin system (6), whereas cyclization of the corresponding tert-butyldimethylsilyl ether 5 afforded selectively the C (1)-diastereomeric product 7.

Scheme 1

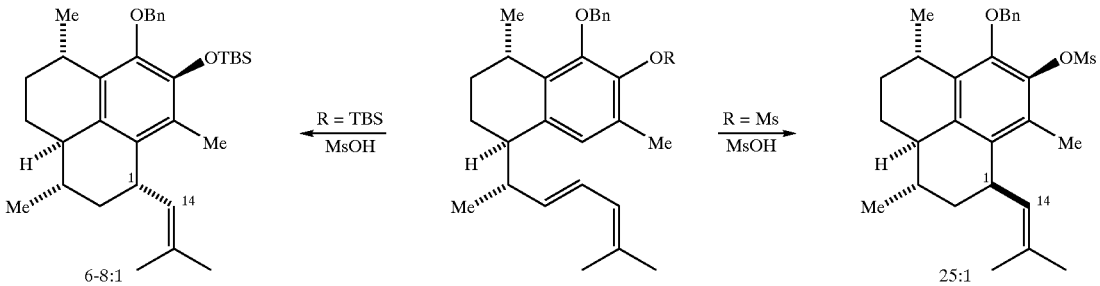

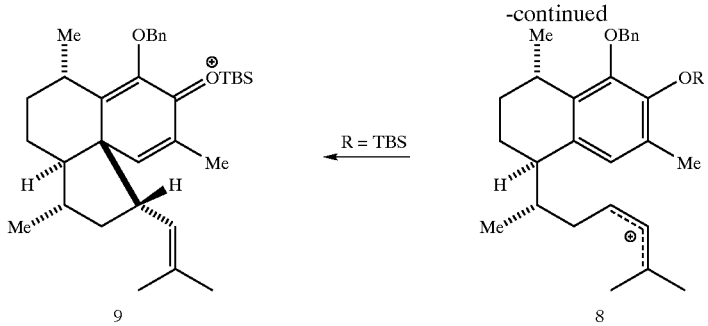

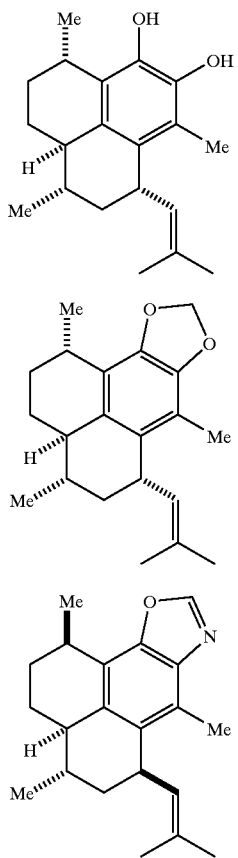

By exploiting the versatile acid-catalyzed cyclization of dienes such as 4 and 5, selective syntheses of both pseudopterosin G-J aglycone 15 and the potent cytotoxic agent helioporin E (16) have been accomplished as set forth herein. It is possible that the reported structure 18 for the related natural product pseudopteroxazole,[21] may also require revision in line with 15 and 16.

Surprisingly, these syntheses provided the first compelling evidence that these compounds are diastereomeric at C (1) relative to the pseudopterosins A-F, not at C (7) as originally reported. Thus, 15 and 16 best represents the stereochemical configurations of pseudopterosin G-J aglycone and helioporin E.

One preferred embodiment of the present invention is a new process for the synthesis of pseudopterosin compounds which has a number of advantages over previously known methods; including (1) an inexpensive chiral starting material (limonene), (2) the use of common or readily available reagents, (3) stereocontrol, (4) simplicity of execution, (5) good yields, and (6) directness. In addition, this synthesis illustrates a number of new and potentially widely useful synthetic methods of noteworthy aspects of stereocontrol and site selectivity.

The present invention is thus directed to the synthetic processes outlined in Schemes 1 2 and 3, to the novel intermediates recited therein, and to the uses of these compounds as synthetic precursors to the pseudopterosins. Other embodiments and aspects of the present invention include the novel synthetic procedures described herein, as detailed below.

DETAILED DESCRIPTION OF THE PREFERRED EMBODIMENTS

The present invention may thus be readily understood in terms of two different reaction pathways. In the synthesis of 6, the 6-membered ring is likely formed by direct electrophilic attack by the intermediate allyl cation 8 on the benzenoid ring at the carbon para to benzyloxy. On the other hand, the transformation 5→7 probably occurs from 8 via the spiro intermediate 9.

Figure 1:
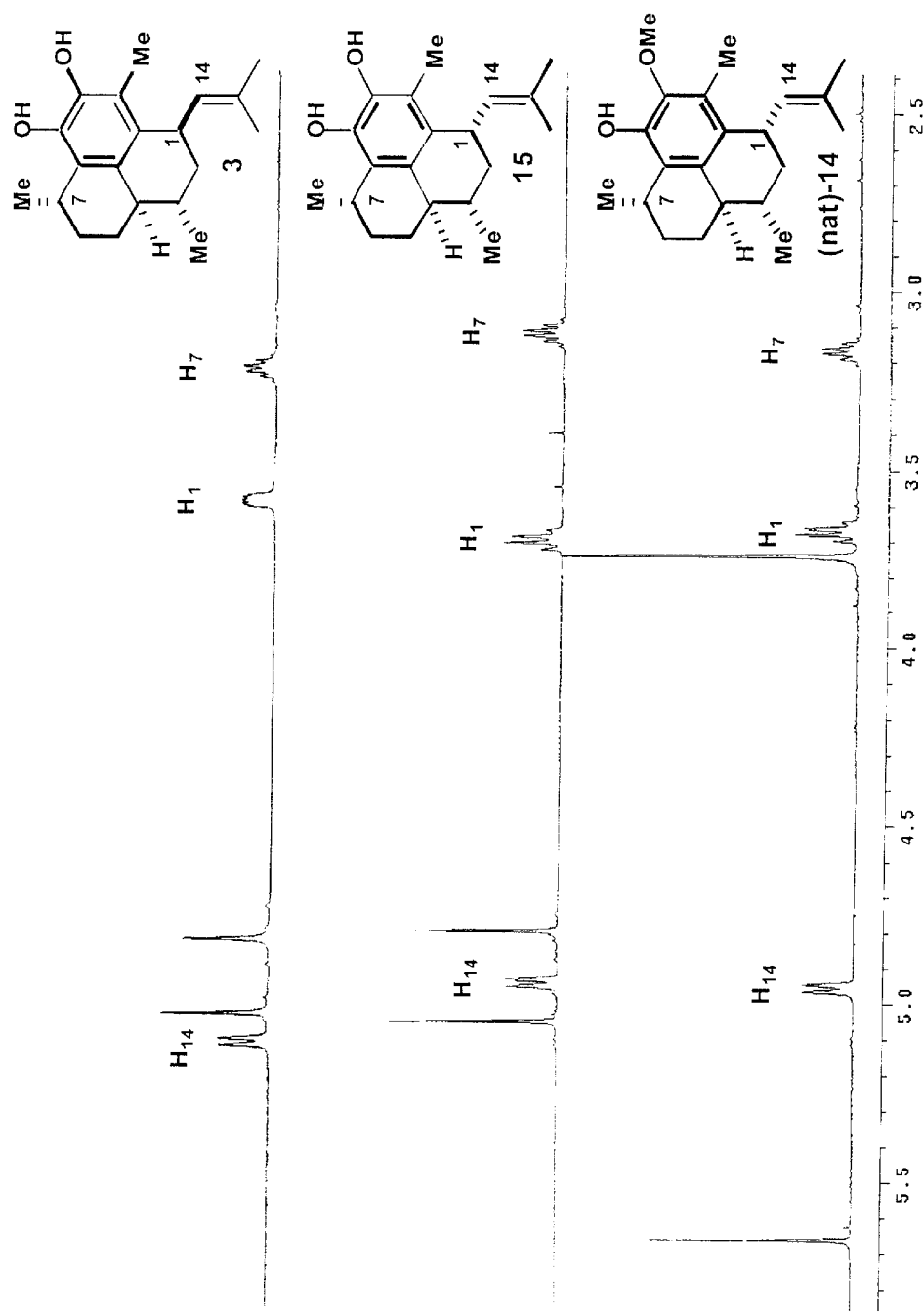
FIG. 1 is the $^1$H NMR data for the fully deprotected cyclization products, aglycones 3 and 15.

The $^1$H NMR spectra of 6 and 7 display a few small but characteristic differences with respect to the protons attached to C (1) and C (14). As expected, the pseudo-axial C (1) proton in 7 shows large couplings and resembles a broad doublet of doublets. In contrast, the pseudo-equatorial C (1) proton in 6 shows small couplings and appears as a compressed multiplet. In addition, the proton attached to C (14) has a chemical shift of 4.97 ppm in 7, whereas the corresponding C (14) proton in 6 appears at 5.11 ppm.[3] These differences are especially apparent from the $^1$H NMR data for the fully deprotected cyclization products, aglycones 3[4] and 15[5] as shown in FIG. 1.

Here it is shown that these $^1$H NMR data, which clearly distinguish the known structures 3 and 15, allow a reassignment of stereochemistry to the previously reported pseudopterosins G-J[6,7] and also helioporin E.[8] The aglycone corresponding to these previously reported structures for pseudopterosins G-J, which is shown as formula 10 below, differs from the pseudopterosin A-F aglycone 3 at the C (7) stereocenter. Similarly, the structure previously ascribed to helioporin E (formula 11 below) also differs from 3 with regard to configuration at C (7).

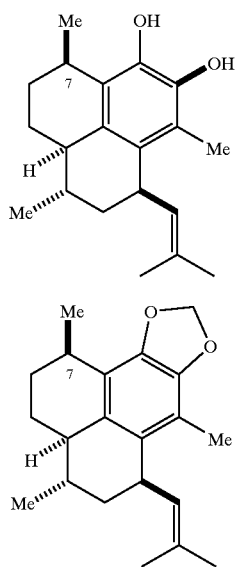

15

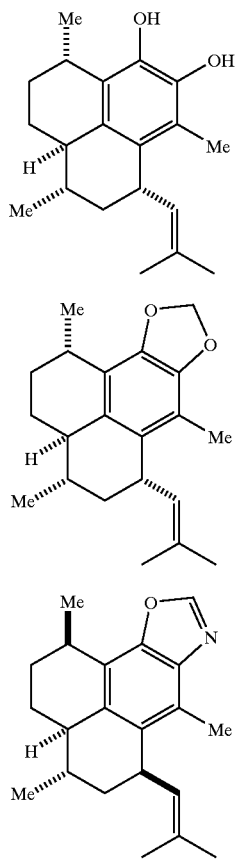

16

18

Careful comparisons of the ¹H NMR data in FIG. 1 for 3 and 15 with the data reported for pseudopterosins G-J[9] suggested that these pseudopterosins might correspond stereochemically to 15.[10]

This hypothesis is consistent with recent synthetic work by Schmalz and co-workers, which showed that the stereochemistries of at least two members of the helioporins, a class of biologically active diterpenoids, were similarly misassigned at C (7).[11] These discoveries left the stereochemical configurations of both helioporin A and helioporin E ambiguous.

Analysis of the ¹H NMR spectrum reported for helioporin E (11) suggested that it too might correspond stereochemically with 15.

To test these proposals cyclization product 7 was converted into its mono-methyl ether 14 by the following sequence: (1) desilylation using $Bu_4NF$ in THF, (2) careful preparative TLC purification to give phenol 12 in >25:1 purity at C (1), (3) alkylation of the C (10) oxygen using methyl iodide under phase-transfer conditions and (4) treatment with lithium di-t-butylbiphenylide (LDBB)[12] to effect debenzylation (i.e., 12→13→14, Scheme 2).

Scheme 2

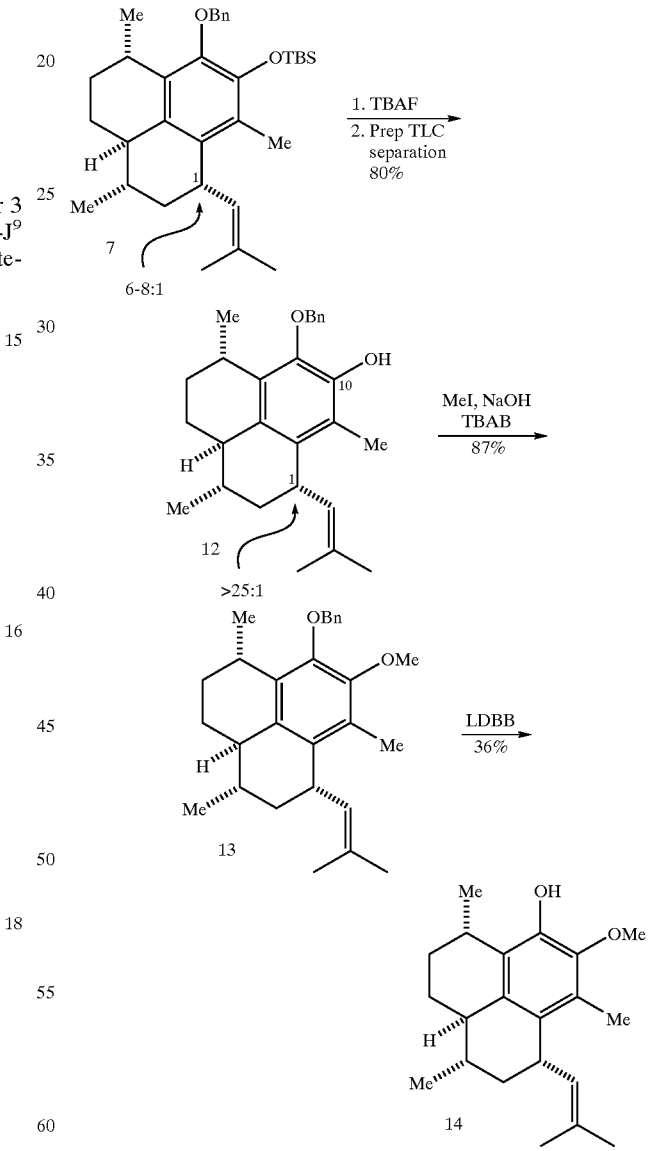

When mono-methyl ether 14 prepared in this way was compared with the corresponding methylated aglycone derived from pseudopterosin I,[13] the samples were found to be identical by ¹H NMR, ¹³C NMR, FTIR, and high-resolution mass spectroscopy.[14]

Thus, the tricyclic core of pseudopterosins G-J must correspond stereochemically with cyclization product 7, and are not diastereomeric at C(1) and C(7) as reported.[15] The ¹H NMR spectrum for the naturally derived version of mono-methyl ether 14 is displayed in FIG. 1. Its correspondence with synthetic aglycone 15 is evident.

The original stereochemical assignment of helioporin E was based primarily on spectral comparisons with pseudopterosins G-J,[16] which implies that helioporin E had been similarly misassigned. To prove this, phenol 12 was converted into the corresponding acetal 16 (Scheme 3).

Scheme 3

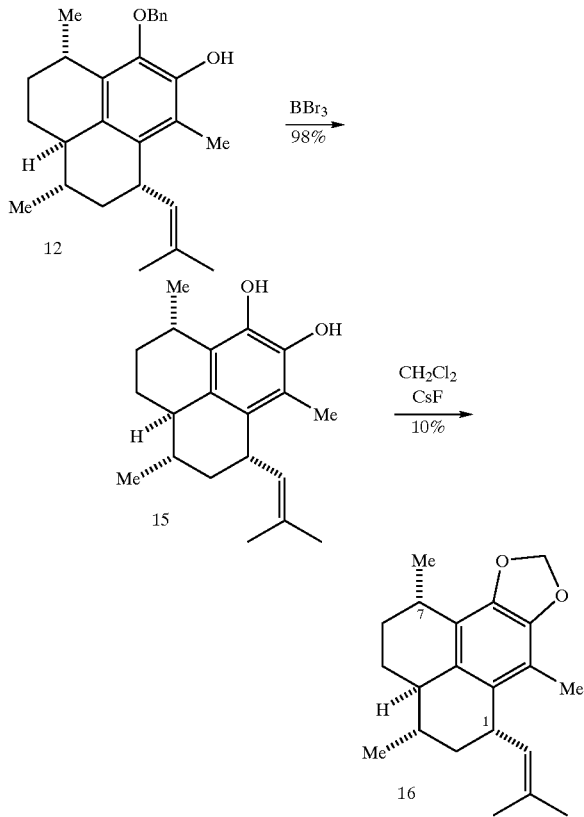

This was accomplished by boron tribromide-mediated debenzylation of 12 to give pseudopterosin G-J aglycone 15, which was methylenated with methylene chloride and cesium fluoride in DMF at 110° C. for 45 min.[17] to produce the desired acetal 16, which was found to be identical to helioporin E by ¹H NMR, FTIR, and high-resolution mass spectroscopy.[18] Thus, the revised structure of helioporin E (16 as shown in Scheme 3) also differs at both C (1) and C (7) as compared with the reported structure.

Figure 2:
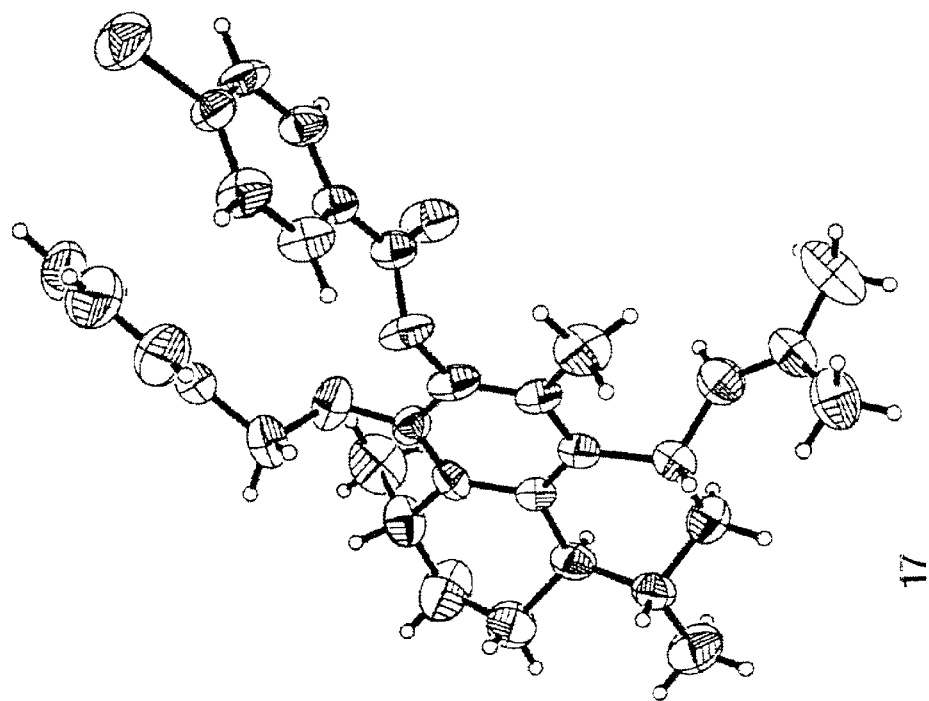
FIG. 2 is the X-ray crystal structure of p-bromobenzoate 17.

Finally, to provide conclusive proof for the stereo chemical reassignment for both pseudopterosin G-J aglycone 15 and helioporin E (16), the p-bromobenzoate 17 of synthetic intermediate phenol 12 was prepared, crystallized, and subjected to analysis, which unambiguously yielded the structure shown below and the X-ray structure shown in FIG. 2.[19]

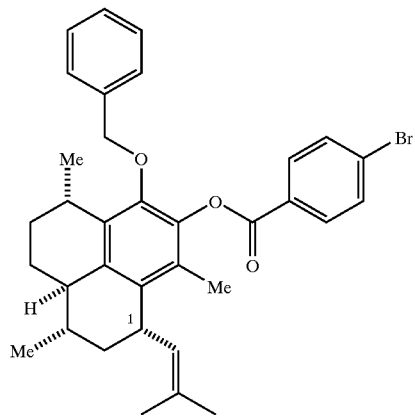

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

General Experimental Methods and Materials

All moisture and air sensitive reactions were performed in oven or flame dried glassware equipped with rubber septa under a positive pressure of nitrogen or argon. When necessary, solvents and reagents were distilled prior to use and were transferred using a syringe or cannula. Reaction mixtures were magnetically stirred, unless otherwise noted. Thin layer chromatography was performed on Merck pre-coated silica gel F-254 plates (0.25 mm). Concentration in vacuo was generally performed using a Büchi rotary evaporator. Kugelrohr distillation temperatures are reported as oven temperatures. Flash column chromatography was performed on Baker 230–400 mesh silica gel.

Physical Data:

Melting points were determined using a Fisher-Johns hot stage apparatus and are reported uncorrected for all crystalline products.

Optical rotations were determined using a Perkin-Elmer 241 polarimeter. Infrared spectra were recorded on a Nicolet 5ZDX FT-IR.

Proton nuclear magnetic resonance spectra (1H NMR) were recorded on an AM-500 (500 MHz), AM-400 (400 MHz), AM-300 (300 MHz) or AM-250 (250 MHz) Bruker nuclear magnetic resonance spectrometer, or a Unity/Inova-500 (500 MHz), Mercury-400 (400 MHz), or Mercury-300 (300 MHz) Varian nuclear magnetic resonance spectrometer, at the frequency indicated. Chemical shifts for ¹H NMR spectra are reported as δ in units of parts per million (ppm) downfield from tetramethylsilane (δ 0.0) using the residual solvent signal as an internal standard: benzene-$d_6$ (δ 7.15, singlet), chloroform-d (δ 7.26, singlet). Multiplicities are given as: br (broad), s (singlet), d (doublet), t (triplet), q (quartet), quint (quintet), sext (sextet) or sept (septet) or m (multiplet). Coupling constants are reported as a J value in Hertz (Hz). The number of protons (n) for a given resonance is indicated by nH.

Carbon nuclear magnetic resonance spectra (¹³C NMR) were recorded on an AM-400 (100 MHz), Mercury-400 (100 MHz), AM-500 (125 MHz), or Inova-500 (125 MHz) spectrometer at the frequency indicated. Chemical shifts for ¹³C NMR spectra are reported as δ in units of parts per million (ppm) downfield from tetramethylsilane (δ 0.0) using the residual solvent signal as an internal standard: benzene-d$_6$ (δ 128.0, triplet), chloroform-d (δ 77.07, triplet).

Electron impact (EI) with an electron beam energy of 70 eV, chemical ionization (CI) with ammonia as the reagent gas, or fast atom bombardment (FAB) in 3-nitrobenzyl alcohol (NBA) with NaI were used for the generation of the [M]$^+$, [M+H]$^+$, [M+NH$_4$]$^+$, or [M+Na]$^+$ ions. Low resolution EI and CI mass spectra were obtained using an AX-505H mass spectrometer (JEOL USA, Inc., Peabody, Mass.) using a mass resolution of 1,500.

High resolution EI and CI mass spectra were obtained by using a SX-102A mass spectrometer (JEOL USA, Inc., Peabody, Mass.) using a mass resolution of 10,000 (EI) and 5,000 (CI). Low and high resolution FAB mass spectra were obtained by using a SX-102A mass spectrometer (JEOL USA, Inc., Peabody, Mass.) using a mass resolution of 3,000 (low resolution) and 10,000 (high resolution). Low and high resolution electrospray mass spectra (ESI) were obtained by using an LCT mass spectrometer (Micromass Inc., Beverly, Mass.) using a mass resolution of 5,000. All mass spectral analyses are reported in units of mass to charge (m/e).

Materials:

Commercial solvents and reagents were used without further purification with the exceptions noted below. For a compilation of methods for the purification of common laboratory substances, see: Perrin, D. D.; Arniarego, W. L. F., Purification of Laboratory Chemicals, Fourth ed.; Butterworth Heinemann: Oxford, 1996.

Solvents:

Methylene chloride was distilled from calcium hydride or from phosphorous pentoxide under nitrogen. Tetrahydrofuran (THF) was distilled from sodium benzophenone ketyl under nitrogen. Dimethylformamide (DMF) was distilled over activated molecular sieves.

Reagents:

Methanesulfonic acid (MsOH) and iodomethane were distilled neat. Lithium di-t-butylbiphenylide was prepared by sonication of lithium metal in a solution of dit-butylbiphenyl in THF for 24 h. Boron tribromide was distilled over calcium hydride.

Molecular sieves (m.s.) were dried by heating them in a microwave oven for 2 mm, placing them at 1 mm Hg for 10 mm, and repeating this procedure three additional times.

EXAMPLE 1

Tricycle 7

TBS ether 5 (0.0228 g, 0.045 mmol) was azeotropically dried with benzene (1 mL), dissolved in CH$_2$Cl$_2$ (4.5 mL) and cooled to −78° C. The clear solution was treated dropwise with methanesulfonic acid (0.0088 mL, 0.14 mmol) in CH$_2$Cl$_2$ (0.1 mL) upon which the solution turned yellow. After warming to −50° C., the mixture was stirred for 4 h and subsequently quenched by dropwise addition of triethylamine (0.2 mL). The resulting clear solution was warmed to ambient temperature and filtered through a small plug of silica gel (hexanes-Et$_2$O, 90:10), to afford after concentration 0.0222 g (97%) of the desired tricycle 7 as a clear oil (6:1 mixture of inseparable diastereomers): R$_f$=0.69 (hexanes-Et$_2$O, 50:50); FTIR (film) 2953, 2928, 2859, 1456, 1428, 840 cm$^{-1}$; $^1$H NMR of the major diastereomer (400 MHz, CDCl$_3$) δ 7.18 (m, 5H), 5.12 (d, J 8.0 Hz, 1H), 4.97 (br d, J=9.2 Hz, 1H), 4.64 (d, J=7.6 Hz, 1H), 3.67 (m, 1H), 3.08 (sext, J=7.2 Hz, 1H), 2.08–1.98 (m, 3H), 2.03 (s, 3H), 1.95 (m, 1H), 1.72 (s, 3H), 1.68 (s, 3H), 1.28 (d, J=7.2 Hz, 3H), 1.27–1.20 (m, 3H), 1.02 (d, J=5.2 Hz, 3H), 0.96 (s, 9H), 0.85 (m, 1H), 0.11 (s, 3H), 0.04 (s, 3H); FABMS (NBA+ NaI) 527 [M+Na]$^+$; HRMS calcd for [C$_{33}$H$_{48}$O$_2$Si+Na]$^+$: 527.3321, found: 527.3315.

EXAMPLE 2

Phenol 12

A solution of TBS ether 7 (0.0222 g, 0.0440 mmol, 6:1 mixture of diastereomers) in THF (2 mL) was treated dropwise with tetrabutylammonium fluoride (0.053 mL, 1.0 M in THF, 0.053 mmol). After five minutes at 23° C., the orange solution was concentrated onto a small amount of silica gel and purified by flash chromatography (hexanes-Et$_2$O, 95:5) to afford 0.0167 g of crude phenol 12 as a clear oil (6:1 mixture of diastereomers). A second careful purification using preparative TLC (hexanes-CH$_2$Cl$_2$, 75:25, allowing the compound to run up 4 times) afforded 0.0137 (80%) phenol 12 as a ≧25:1 mixture of diastereomers (as determined by $^1$H NMR analysis): R$_f$=0.43 (hexanes-Et$_2$O, 85:15); [α]$^D_{25}$+103 (c 0.20, CHCl$_3$); FTIR (film) 3526, 2920, 2862, 1452, 1050 cm$^{-1}$; $^1$H NMR (500 MHz, CDCl$_3$) δ 7.42 (m, 5H), 5.51 (s, 1H), 4.97 (d, J=11.2 Hz, 2H), 4.73 (d, J=11.2 Hz, 1H), 3.74 (m, 1H), 3.24 (sext, J=7.3 Hz, 1H), 2.10 (m, 3H), 2.06 (s, 3H), 2.01 (m, 1H), 1.74 (s, 3H), 1.67 (s, 3H), 1.36 (m, 1H), 1.34 (d, J=6.8 Hz, 3H), 1.25 (m, 2H), 1.03 (d, J=5.9 Hz, 3 H), 0.97 (m, 1H); $^{13}$C NMR (100 MHz, CDCl$_3$) δ 145.3, 142.3, 137.3, 135.1, 131.8, 131.2, 131.0, 128.7, 128.5, 128.3, 127.9, 121.0, 75.3, 43.8, 40.2, 37.1, 34.6, 31.6, 29.3, 27.8, 25.6, 23.8, 20.1, 17.7, 12.1; CIMS (NH$_3$) 408 [M+NH$_4$]~. 391 [M+H]$^+$; HRMS calcd for [C$_{27}$H$_{34}$O$_2$+H]$^+$: 391.2637, found: 391.2622.

EXAMPLE 3

Methyl Ether 13

A solution of phenol 12 (0.0020 g, 0.005 1 mmol) in THF (0.5 mL) was treated with iodomethane (0.003 mL, 0.05 mmol), potassium hydroxide (0.006 g, 0.1 mmol), tetrabutylammonium bromide (0.002 g, 0.005 mmol) and stirred at 23° C. for 1 h. The reaction mixture was concentrated onto a small amount of silica gel and purified by flash chromatography (hexanes-Et$_2$O, 95:5) to afford 0.0018 g (87%) of desired product 13 as a clear oil: R1=0.51 (hexanes-Et2O, 90:10); [α]$_D^{23}$+28 (c 0.18, CHCl$_3$); FTIR (film) 2925, 2862, 1453, 1315, 1063, 1025 cm$^{-1}$; $^1$H NMR (500 MHz, CDCl$_3$) δ 7.49 (d, J=7.8 Hz, 2H), 7.39 (t, J=7.3 Hz, 2H), 7.32 (t, J=7.3 Hz, 1H), 5.08 (d, J=11.2 Hz, 1H), 4.98 (br d, J=9.8 Hz, 1H), 4.94 (d, J=11.2 Hz, 1H), 3.79 (s, 3H), 3.72 (m, 1H), 3.25 (sext, J=7.3 Hz, 1H), 2.10 (s, 3H), 2.05 (m, 3H), 1.96 (m, 1H), 1.74 (s, 3H), 1.69 (s, 3H), 1.36–1.20 (m, 3H), 1.26 (d, J=6.8 Hz, 3H), 1.03 (d, J=5.9 Hz, 3H), 0.90 (m, 1H); $^{13}$C NMR (100 MHz, CDCl$_3$) δ 149.6, 147.8, 138.5, 135.5, 134.3, 133.6, 130.9, 128.6, 128.4, 128.3, 127.7, 127.6, 74.3, 60.3, 44.1, 40.2, 37.5, 34.2, 31.2, 28.5, 27.7, 25.6, 24.6, 20.6, 17.7, 12.3; EIMS 404 [M]$^+$; HRMS calcd for [C$_{28}$H$_{36}$O$_2$]$^+$: 404.2715, found: 404.2722.

EXAMPLE 4

Methyl Ether 14

A solution of methyl ether 13 (0.0018 g, 0.0044 mmol) in THF (0.5 mL) was cooled to −78° C. and treated with a solution of lithium-di-tert-butylbiphenylide (0.450 mL, ~0.25 M in THF, 0.11 mmol) until the color stayed dark green. After five minutes the reaction mixture was quenched with NH$_4$Cl (saturated aq, 1 mL) and warmed to ambient temperature. Water was added and the mixture was extracted twice with ether. The combined organic extracts were dried over MgSO$_4$ (anhyd), filtered and concentrated in vacuo. Flash chromatography (hexanes→hexanes-Et$_2$O, 95:5) afforded 0.0005 g (36%) of desired product 14 as a clear film: R$_f$=0.36 (hexanes-EtOAc, 90:10); [α]$_D^{25}$+90 (c 0.05, CHCl$_3$); FTIR (film) 3419, 2953, 2923, 2862, 1455, 1298, 1260, 1119, 1058, 1018 cm$^{-1}$; $^1$H NMR (500 MHz, CDCl$_3$) δ 5.66 (s, 1H), 4.95 (br d, J=9.3 Hz, 1H), 3.74 (s, 3H), 3.67 (m, 1H), 3.16 (m, 1H), 2.16 (m, 1H), 2.08 (s, 3H), 2.07–1.99 (m, 2H), 1.96 (m, 1H), 1.73 (s, 3H), 1.67 (s, 3H), 1.67 (s, 3H), 1.36–1.18 (m, 3H), 1.29 (d, J=6.8 Hz, 3H), 1.02 (d, J=5.9 Hz, 3H), 0.94 (m, 1H); $^{13}$C NMR (100 MHz, CDCl$_3$) δ 131.1, 128.4, 60.8, 44.8, 40.3, 37.1, 34.1, 32.2, 28.9, 27.9, 25.6, 23.1, 20.1, 17.7, 12.6; EIMS 314 [M]$^+$, 258, 243, 201; HRMS calcd for [C$_{21}$H$_{30}$O$_2$]$^+$: 314.2246, found: 314.2242.

EXAMPLE 5

Pseudopterosin G-J Aglycone 15

A solution of phenol 12 (0.0024 g, 0.0061 mmol) in CH$_2$Cl$_2$ (1 mL) was cooled to 0° C. and treated dropwise with a solution of BBr$_3$ (0.00087 mL, 0.0092 mmol) in CH$_2$Cl$_2$ (0.050 mL). After five minutes, the reaction mixture was concentrated onto a small amount of silica gel and purified by flash chromatography (hexanes: EtOAc, 90:10→hexanes: EtOAc, 50:50) to afford 0.0018 g (98%) of desired catechol 15 as a light yellow film, which was taken immediately on to the next step: R$_f$=0.26 (hexanes-EtOAc, 80:20); $^1$H NMR (500 MHz, CDCl$_3$) δ 5.05 (s, 1H), 4.94 (br d, J=9.3 Hz, 1H), 4.79 (s, 1H), 3.69 (m, 1H), 3.12 (m, 1H), 2.20 (m, 1H), 2.08–1.94 (m, 3H), 2.04 (s, 3H), 1.73 (d, J=1.0 Hz, 3H), 1.67 (d, J=1.0 Hz, 3H), 1.38–1.18 (m, 3H), 1.28 (d, J=6.8 Hz, 3H), 1.02 (d, J=5.9 Hz, 3H), 0.92 (m, 1H).

EXAMPLE

Helioporin E (16)

Catechol 15 (0.0018 g, 0.0060 mmol) was dissolved in DMF (0.25; mL) (deoxygenated by the freeze-pump-thaw method (three times) and treated with CsF (0.049 g, 0.32 mmol) and CH$_2$Cl$_2$ (0.0045 mL, 0.070 mmol). The reaction mixture was flushed with nitrogen, sealed in a screw-top glass vial, and heated to 110° C. After stirring for 40 minutes, the reaction mixture was passed through a small plug of silica gel (hexanes-Et$_2$O, 90:10) and purified by preparative TLC (hexanes-Et$_2$O, 99:1, run up twice) to afford 0.0002 g (10%) of desired tetracycle 16 as a clear film: R$_f$=0.53 (hexanes-Et2O, 95:5); FTIR (film) 2955, 2921, 2856, 1453, 1421, 1085, 1027 cm$^{-1}$; $^1$H NMR (500 MHz, CDCl$_3$) δ 5.90 (d, J=1.5 Hz, 1H), 5.84 (d, J=1.5 Hz. 1H), 4.94 (br d, J=9.3 Hz, 1H), 3.71 (br q, J=8.8 Hz, 1H), 2.96 (m, 1H), 2.15–1.97 (m, 4H), 2.03 (s, 3H), 1.72 (s, 3H), 1.67 (s, 3H), 1.30 (d, J=6.8 Hz, 3H), 1.30–1.11 (m, 3H), 1.00 (d, J=5.4 Hz, 3H), 1.00 (m, 1H); ELMS 312 [M]$^+$, 256, 241; HRMS calcd for [C$_{21}$H$_{28}$O$_2$]$^+$: 312.2090, found: 312.2091.

EXAMPLE p-Bromobenzoate 17

A solution of phenol 12, (0.001 g, 0.003 mmol), purified by preparative TLC to ≧99:1 as judged by $^1$H NMR, in CH$_2$Cl$_2$ was treated with p-dimethyl-aminopyridine (excess, approx. 0.005 g) and p-bromobenzoyl chloride (excess, approx. 0.005 g). After stirring for 20 mm, the reaction mixture was purified by preparative TLC (hexanes-Et$_2$O, 90:10) to afford 0.001 g (70%) of desired product 17, which after concentration from methanol solidified to a white powder. Clear X-ray quality crystals were grown by slow evaporation from methanol: mp 140–144° C.; R$_f$=0.39 (hexanes-Et$_2$O, 90:10); FTIR (film) 1741, 1265, 1115, 1075, 1011 cm$^{-1}$; $^1$H NMR (500 MHz, CDCl$_3$) δ 7.99 (d, J=8.3 Hz, 1H), 7.59 (d, J 8.3 Hz, 1H), 7.19 (s, 5H), 5.03 (br s, 1H), 4.88 (br s, 2H), 3.74 (m, 1H), 3.21 (br s, 1H), 2.26–1.95 (m, 4H), 1.98 (s, 3H), 1.71 (s, 3H), 1.66 (s, 3H), 1.45–1.22 (m, 4H), 1.26 (d, 3H), 1.05 (d, 5.9 Hz, 3H), 0.98 (m, 1H); FABMS (NBA+NaI) 597 [M+Na+2]$^+$, 595 [M+Na]$^+$; HRMS calcd for [C$_{34}$H$_{37}$BrO$_3$+Na]$^+$: 595.1824, found: 595.1832.

The following references have been cited herein as background information related to this application. To the extent necessary for a complete understanding of the invention, the disclosures of these publications are hereby incorporated herein by reference:

(1) See also, Corey, E. J.; Lazerwith, S. E. *J. Am. Chem. Soc.* 1998, 120, 12777.

(2) For other synthetic routes to the pseudopterosin family see (a) Broka, C. A.; Chan, S.; Peterson, B. *J. Org. Chem.* 1988, 53, 1584. (b) Corey, E. J.; Carpino, P. *J. Am. Chem. Soc.* 1989, 111, 5472. (c) Corey, E. J.; Carpino, P. *Tetrahedron Lett.* 1990, 31, 3857. (d) McCombie, S. W.; Cox, B.; Lin, S. -I.; Ganguly, A. K.; McPhail, A. T. *Tetrahedron Lett.* 1991, 32, 2083. (e) McCombie, S. W.; Ortiz, C.; Cox, B.; Ganguly, A. K. *Synlett* 1993, 541. (f) Buszek, K. R. *Tetrahedron Lett.* 1995, 36, 9125. (g) Buszek, K. R.; Bixby, D. L. *Tetrahedron Lett.* 1995, 36, 9129. (h) Gill, S.; Kocienski, P.; Kohler, A.; Pontiroli, A.; Qun, L. *J. Chem. Soc., Chem. Commun.* 1996, 1743. (i) Majdalani, A.; Schmalz, H. -G. *Tetrahedron Lett.* 1997, 38, 4545. (j) Majdalani, A.; Schmalz, H. -G. *Synlett* 1997, 1303. (k) Kato, N.; Zhang, C. -S.; Matsui, T.; Iwabachi, H.; Mori, A.; Ballio, A.; Sassa, T. *J. Chem. Soc., Perkin Trans.* 1 1998, 2475.

(3) In these cases, the peak shapes are similar broad doublets with couplings of approx. 9 Hz.

(4) 3 arises from the deprotection of 6 (see reference 1).

(5) 15 arises via the deprotection of 7 (see Schemes 2 and 3).

(6) Roussis, V.; Wu, Z.; Fenical, W.; Strobel, S. A.; Van Duyne, G. D.; Clardy, J. *J. Org. Chem.* 1990, 55, 4916.

(7) Pseudopterosins G-J were originally assigned to be C (7) diastereomers of pseudopterosins A-F by NOE experiments. See reference 6.

(8) For isolation and original structural determination of the helioporins see: Tanaka, J.; Ogawa, N.; Liang, J.; Higa, T.; Gravalos, D. G. *Tetrahedron* 1993, 49, 811. For structural revision of helioporin C and D see: (a) Geller, T.; Schmalz, H. G.; Bats, J. W. *Tetrahedron Lett.* 1998, 39, 1537. (b) Hörstermann, D.; Schmalz, H. G.; Kociok-Köhn, G. *Tetrahedron* 1999, 55, 6905.

(9) Shimshock, S. J.; Waltermire, R. E.; DeShong, P. *J. Am. Chem. Soc.* 1991, 113, 8791.

(10) A natural sample of pseudopterosin I was generously donated by Professor William Fenical. It was converted into its methylated aglycone by: (1) treatment with methyl iodide and potassium carbonate in hot acetone to afford a mixture of methylated products (arising from acetyl migration in the sugar portion of the molecule), and (2) deglycosylation with HCl (aq.) in methanol. See reference 6.

(11) Synthetic methyl ether 14: [α]$_D^{25}$+90 (c 0.05, CHCl$_3$). Methyl ether 14 derived from pseudopterosin I: [α]$_D^{25}$+ 98 (c 0.05, CHCl$_3$).

(12) Professor Fenical and co-workers independently discovered indirect evidence for this stereochemical reassignment, but lacked experimental proof (personal communication).

(13) Stereochemical assignments for pseudopterosins G-J were made by NOE. See reference 6.
(14) Clark, J. H.; Holland, H. L.; Miller, J. M. *Tetrahedron Lett.* 1976, 38, 3361.
(15) We are grateful to Professor Tatsuo Higa for copies of the $^1$H NMR spectrum of helioporin E (16).
(16) A similar reassignment was hypothesized by Schmalz and co-workers. See reference 8b.
(17) p-Bromobenzoate 17 was prepared from phenol 12 by treatment with excess p-bromobenzoyl chloride and DMAP in CH$_2$Cl$_2$, followed by preparative TLC purification. Recrystallization from methanol afforded X-ray quality crystals, mp 140–144° C.
(18) Detailed X-ray crystallographic data are available from the Cambridge Crystallographic Data Center, 12 Union Road, Cambridge CB2 1EZ, U.K.
(19) Rodriguez, A. D.; Ramirez, C.; Rodriguez, I. I.; Gonzalez, E. *Org. Lett.* 1999, 1, 527.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. The synthetic process in which the compound of Formula 4 is converted to the compound of Formula 6 by treatment with methanesulfonic acid:

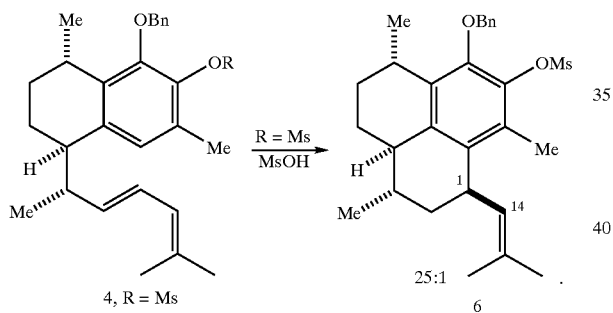

2. The synthetic process in which the compound of Formula 5 is converted to the compound of Formula 7 by treatment with methanesulfonic acid:

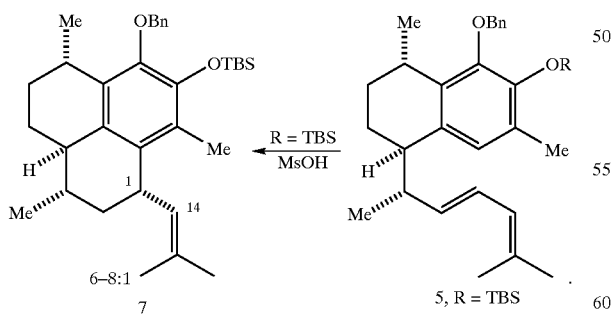

3. The compound of Formula 4:

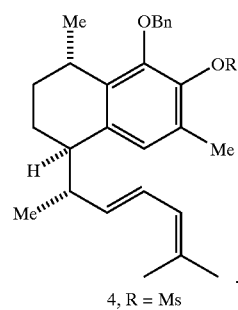

4. The compound of Formula 5:

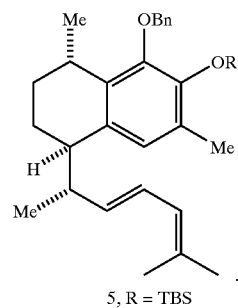

5. The compound of Formula 6:

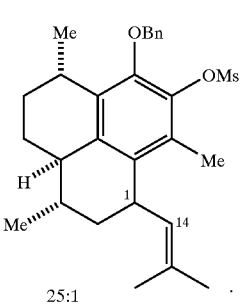

6. The compound of Formula 7:

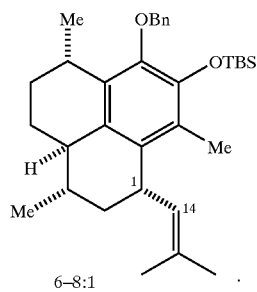

* * * * *